(12) United States Patent
Leyer et al.

(10) Patent No.: US 9,354,217 B2
(45) Date of Patent: May 31, 2016

(54) WATER ANALYSIS SENSOR CARTRIDGE WITH TRANSPORT CONTAINER

(75) Inventors: Axel Leyer, Moenchengladbach (DE); Lothar Heidemanns, Korschenbroich (DE); Andreas Jonak, Meerbusch (DE); Markus Hahn, Kempen (DE); Heinz Rudde, Hueckelhoven (DE); Claudia Rieger, Duesseldorf (DE); Aurelia Stellmach-Hanulok, Wuelfrath (DE); Andreas Golitz, Moers (DE); Michael Kussmann, Duesseldorf (DE)

(73) Assignee: HACH LANGE GMBH, Berlin (DE)

( * ) Notice: Subject to any disclaimer, the term of this patent is extended or adjusted under 35 U.S.C. 154(b) by 550 days.

(21) Appl. No.: 13/805,667

(22) PCT Filed: Jul. 1, 2010

(86) PCT No.: PCT/EP2010/059332
§ 371 (c)(1),
(2), (4) Date: Jan. 30, 2013

(87) PCT Pub. No.: WO2012/000552
PCT Pub. Date: Jan. 5, 2012

(65) Prior Publication Data
US 2013/0118274 A1  May 16, 2013

(51) Int. Cl.
*G01N 1/12* (2006.01)
*G01N 33/18* (2006.01)
(52) U.S. Cl.
CPC ............ *G01N 33/18* (2013.01); *G01N 33/1886* (2013.01)
(58) Field of Classification Search
CPC ... G01N 1/14; G01N 1/2035; A61B 10/0045; A61B 10/0096; B01L 3/502

USPC ....................................................... 73/864.51
See application file for complete search history.

(56) References Cited

U.S. PATENT DOCUMENTS

| 4,045,296 | A | * | 8/1977 | Sternberg | G01N 27/3271 |
| | | | | | 435/11 |
| 4,469,630 | A | * | 9/1984 | Flashner | C07K 16/065 |
| | | | | | 435/70.21 |
| 4,892,710 | A | * | 1/1990 | Wong | B01D 35/303 |
| | | | | | 210/282 |
| 5,233,860 | A | * | 8/1993 | Mori | G01N 33/1886 |
| | | | | | 436/8 |
| 2005/0261582 | A1 | * | 11/2005 | Becker | A61B 8/06 |
| | | | | | 600/437 |
| 2007/0289779 | A1 | * | 12/2007 | Howard | E21B 17/028 |
| | | | | | 175/40 |
| 2008/0264788 | A1 | * | 10/2008 | Uthemann | G01N 27/283 |
| | | | | | 204/412 |
| 2010/0079751 | A1 | * | 4/2010 | Porat | B01L 3/502 |
| | | | | | 356/300 |

FOREIGN PATENT DOCUMENTS

| DE | 101 51 232 A1 | 5/2003 |
| EP | 0 493 819 A1 | 7/1992 |
| WO | WO 2006/106071 A1 | 10/2006 |

\* cited by examiner

*Primary Examiner* — Eric S McCall
*Assistant Examiner* — Mohammed E Keramet-Amircola
(74) *Attorney, Agent, or Firm* — Norman B. Thot

(57) ABSTRACT

A transport container system for a water analysis sensor cartridge includes a water analysis sensor cartridge configured to be interchangeable. The water analysis sensor cartridge comprises at least two different sensor membranes. A transport container cup comprises, for each of the at least two different sensor membranes, a separate moist chamber. Each separate moist chamber comprises one chamber opening and a specific humectant for each of the at least two different sensor membranes.

24 Claims, 3 Drawing Sheets

WATER ANALYSIS SENSOR CARTRIDGE WITH TRANSPORT CONTAINER

The present invention relates to a transport container system for an interchangeable water analysis sensor cartridge.

Water-analysis immersion probes are used particularly in process analytics for monitoring one or a plurality of analytes in water in order to monitor the quality of the water, e.g. of drinking water or waste water. To facilitate maintenance, immersion probes of the state of the art are of a modular design and consist substantially of a fixedly installed probe base and an exchangeable senor cartridge comprising one or a plurality of different sensors.

Since, over time, the sensors are subject to wear, which will result in an increasing deterioration of the quality of the measurement, it is advisable to make available new and unworn sensors simply be exchanging the sensor cartridge.

The sensor cartridge is relatively sensitive and, depending on their respective type, the sensors and particularly the sensor membranes of the cartridge must not dry out. For this reason, transport of a new, unconsumed sensor cartridge is carried out by storing the sensor in a transport container which includes a specific electrolyte solution, i.e. a humectant.

Sensor cartridges can be equipped with differently selective sensors, i.e. with cation- and/or anion-selective sensor membranes. As a consequence, when such sensor cartridges have been stored in a transport container filled with only one electrolyte solution, the active measurement substances in the sensor membranes, the so-called ionophores, will diffuse into the electrolyte solution. The diffusion of the ionophores of the respective sensor membranes into the electrolyte solution will cause a contamination of the respective other sensor membranes of the sensor cartridge. This contamination generates a chemical change in the sensor membranes, with the consequence that these will react in an erroneous manner on the analytes contained in the water.

In view of the above, it is an object of the present invention to provide a transport container system for an interchangeable water analysis sensor cartridge wherein, during transport in a transport container system, a contamination of the sensor membranes of an interchangeable sensor cartridge is prevented.

According to the invention, the above object is achieved by a transport container system for an interchangeable water analysis sensor cartridge with the features defined in claim 1.

The transport container system for an interchangeable water analysis sensor cartridge consists of an interchangeable water analysis sensor cartridge comprising at least two different sensor membranes, and of a transport container cup comprising, for each sensor membrane, a separate moist chamber with respectively one chamber opening, with the moist chambers comprising a humectant that is specific for the sensor membranes. The humectant is introduced into the moist chamber by way of the chamber opening. Furthermore, the contact between the sensor membranes and the humectant arranged therein is made possible by the chamber opening.

For transport, said interchangeable sensor cartridge will be inserted into the transport container cup. Herein, it is guaranteed that the sensor membranes can be stored separately and in a humectant that is specific for them, thus excluding a contamination of the respective other sensor membrane. Dedicated humectants that are used specifically for the different sensor membranes will guarantee an optimum performance of the sensor membrane immediately after removal, i.e. the sensor cartridge will be immediately ready for use.

Preferably, the separate moist chambers are formed by respectively one substantially vertical chamber wall arranged in vertical orientation on a bottom of the transport-container cup. By way of alternative, there can be provided any other geometric shape of the moist chamber that is complementary to the sensor membranes.

Preferably, at least one specific humectant is an electrolyte gel. Alternatively, at least one specific humectant can be formed by a sponge body soaked with an electrolyte solution. Such a specific humectant will guarantee a hundred-percent air humidity on the sensor membranes which are in direct contact with the humectant.

According to a preferred embodiment, there is provided a liquid-tight transport container lid for liquid-tight closure of the transport container cup. Thus, the interchangeable sensor cartridge can be safely transported and stored without occurrence of a significant deterioration of the sensor membranes. Further, said transport container lid offers protection to the electrical contact sites of the sensor cartridge via which the sensor cartridge is in electrical contact with a probe base.

Preferably, the water analysis sensor cartridge is provided with a surrounding flange which is in liquid-tight abutment on the transport container cup edge, with a transport container lid for fixing the water analysis sensor cartridge being formed as a fixing sleeve. By way of this abutment, the sensor cartridge can be stored in the transport container cup in an optimum manner, i.e. the distance between the sensor membranes and the corresponding moist chambers can be set in such a well-defined fashion that the sensor membrane is respectively in optimum abutment on the humectant. Further, said surrounding flange face also forms an abutment face for connection of the sensor cartridge to a probe base.

According to a preferred embodiment, the transport container cup and the transport container lid are provided with a cooperating bayonet-type lock. A bayonet-type lock is a quickly lockable, reliably holding and easily releasable connection.

Preferably, the transport container lid is on its external side provided with a gripping structure arranged along its periphery, said gripping structure making it easier to seize the lid and particularly allowing for enhanced force-locking between the gripping hand and the transport container lid in the circumferential direction for twisting the lid. Further, also the transport container cup can be provided with said gripping structure so as to generally facilitate the opening of the transport container system.

Preferably, at least one of the sensor membranes of the substantially cylindrical water analysis sensor cartridge is arranged eccentrically in the cartridge. In this manner, optimum use is made of the space within the sensor cartridge for the sensor membranes, thus making it possible to provide a plurality of different sensors in a sole sensor cartridge. In analogy thereto, the transport container cup comprises the same number of moist chambers so that each of the sensor membranes can be stored separately and in a humectant specifically provided for it.

According to a preferred embodiment, the water analysis sensor cartridge and the transport container cup are provided with cooperating anti-twist locks which are realized e.g. in the form of pins extending vertically from the transport container cup edge and which are complementary with corresponding openings in the surrounding flange of the sensor cartridge. Thereby, it is safeguarded that, during transport and/or storage, the sensor membranes of the sensor cartridge in the moist chambers provided for them.

According to a particularly preferred embodiment, the transport container cup includes an absorption agent in the interior of the cup. The absorption agent is always effective with respect to the interior of the cup, even in the state where the sensor cartridge has been inserted into the transport container cup. Preferably, the absorption agent is a sponge body. Alternatively, the absorption agent can consist of a hygroscopic medium such as e.g. silica gel. The absorption agent can be accommodated e.g. in a dedicated chamber arranged centrally on the bottom of the transport container cup. The absorption agent can take up e.g. excess electrolyte solution if this solution issues from out of the moist chambers, so that a mutual mixing of the different electrolyte solutions can be effectively prevented.

An embodiment of the invention will be explained in greater detail hereunder with reference to the drawing.

Figure 1:
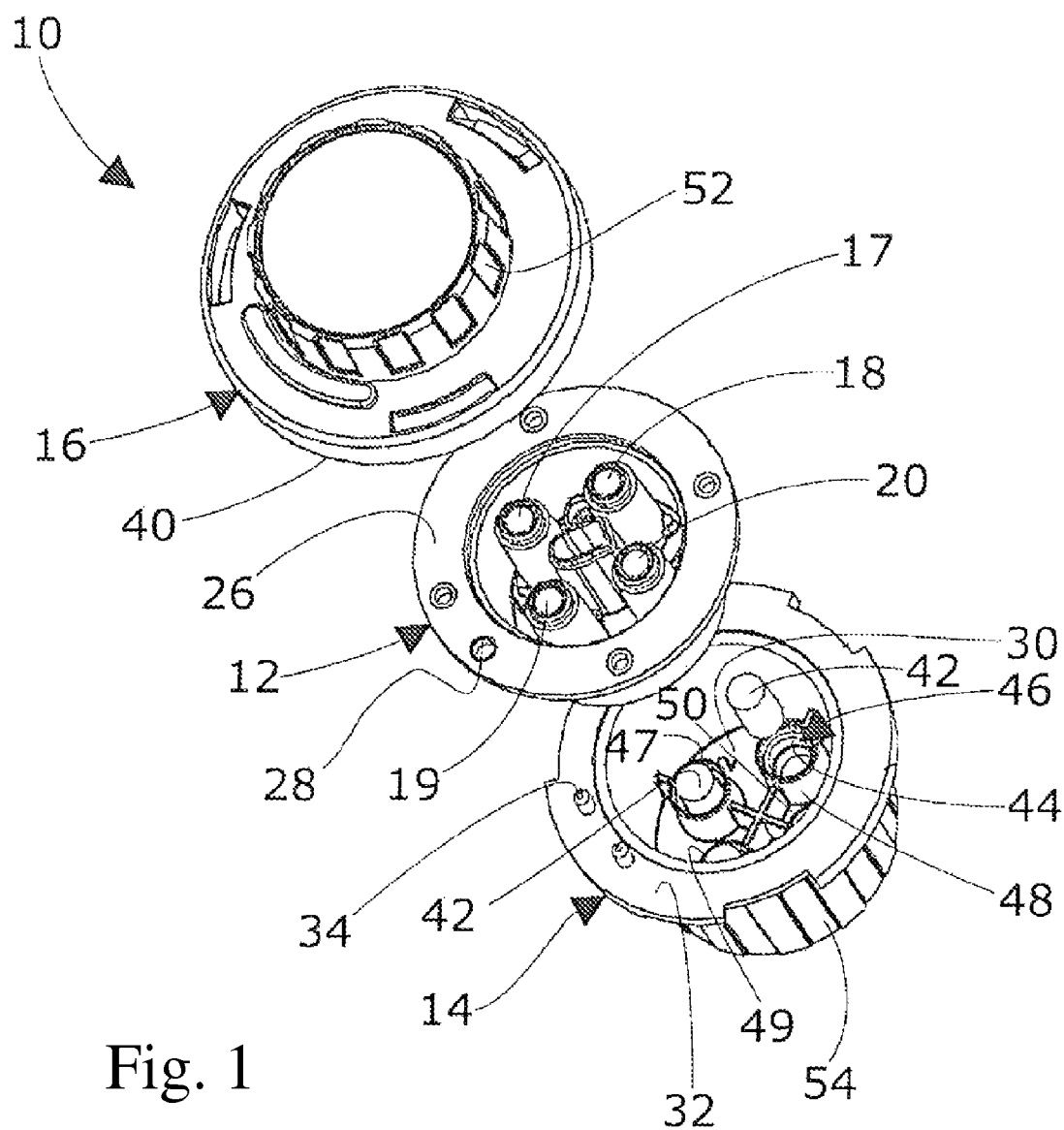
FIG. 1 is an exploded view of the transport container system according to the invention.

In FIG. 1, a transport container system 10 for an interchangeable water analysis sensor cartridge 12 is shown. Said system 10 consists of an interchangeable sensor cartridge 12 which together with a probe base (not shown) forms a water-analysis immersion probe, and of a transport container cup 14 provided for the sensor cartridge 12, said transport container cup 14 being closeable by a transport container lid 16.

Figure 2:
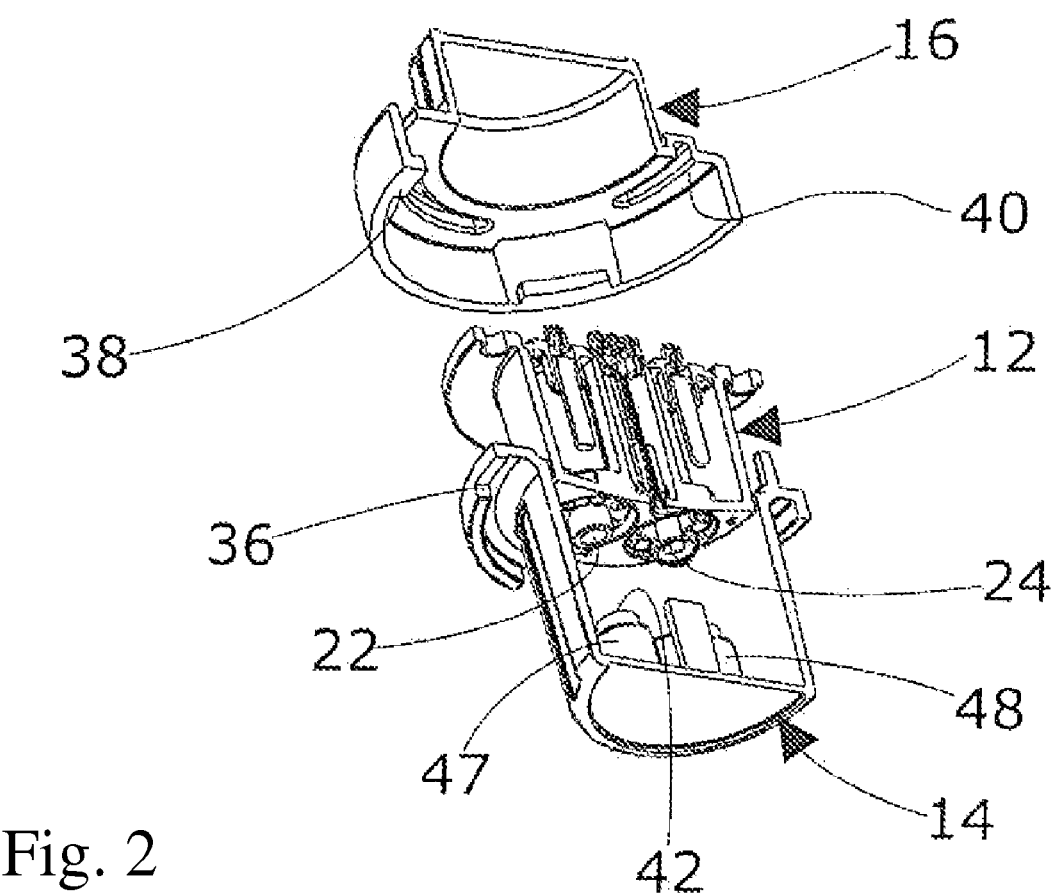
FIG. 2 is a sectional view of the transport container system according to the invention.
Figure 3:
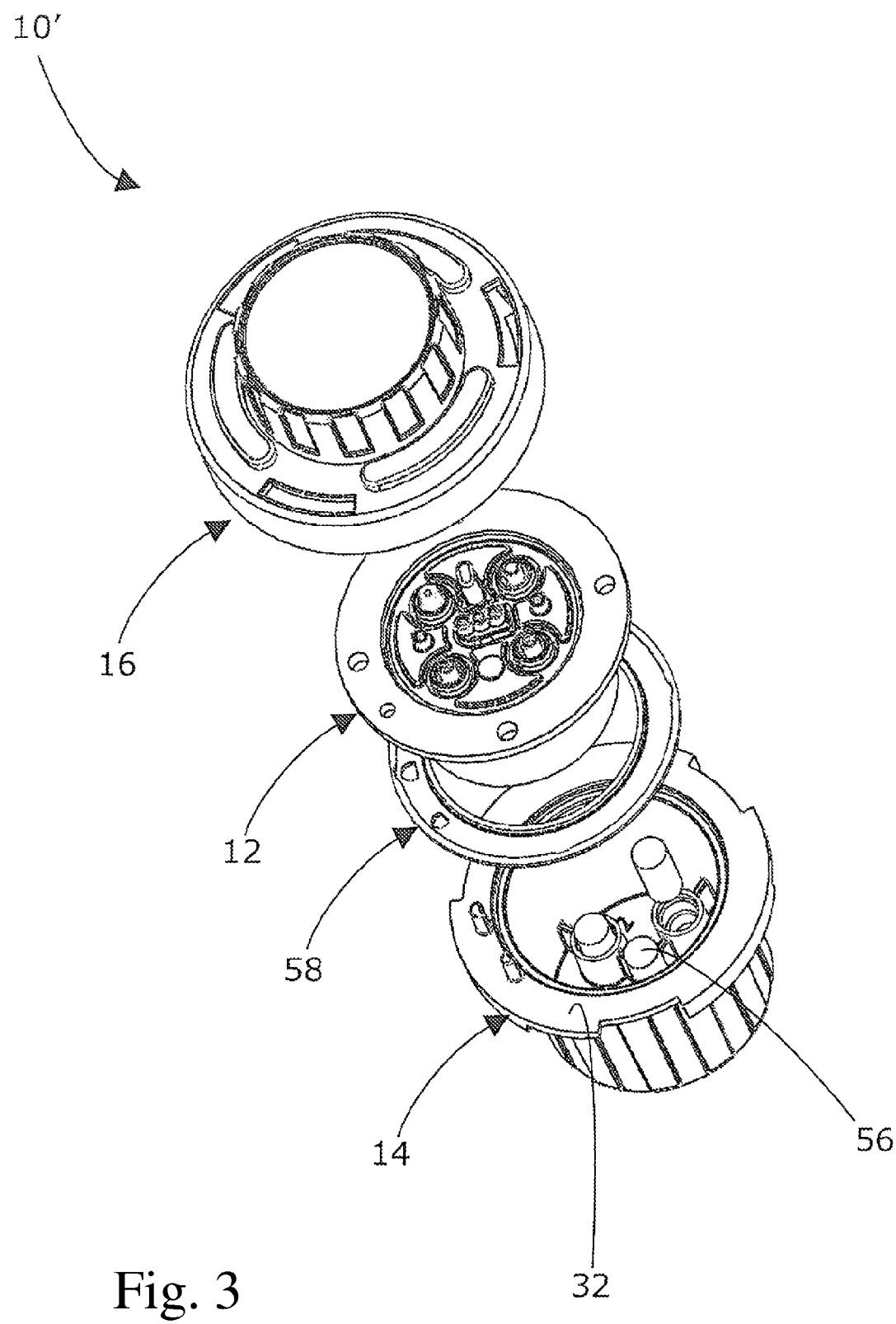
FIG. 3 is an exploded view of an alternative embodiment of the transport container system according to the invention.

Sensor cartridge 12 comprises four different sensors 17, 18, 19, 20. On their distal ends, the four sensors 17, 18, 19, 20 comprise sensor membranes 22, 24 (see FIG. 2). Within the substantially cylindrical sensor cartridge 12, the sensors 17, 18, 19, 20 are arranged eccentrically, thus allowing optimum use of the space in sensor cartridge 12. Further, sensor cartridge 12 comprises a surrounding flange 26 with round openings 28 provided therein.

The substantially cylindrical transport container cup 14 is made of plastic and is closed at its bottom 30. On its other longitudinal end, cup 14 comprises an opening with a flange-like cup edge 32. On cup edge 32, axially extending pins 34 are provided which are adapted to corresponding openings 28 in the flange 26 of sensor cartridge 12 and together form an anti-twist locking assembly. Cup 14 further comprises, on its cup edge 32, a plurality of bayonet elements 36 (see FIG. 2) which together with corresponding bayonet lugs 38 (FIG. 2) of lid 16 form a bayonet lock assembly so that the lid with its flange-like lid edge 40 will be twisted on the flange 26 of sensor cartridge 12.

In its interior, cup 14 comprises separate moist chambers 47, 48, 49, 50 for each of the sensor membranes 22, 24 of sensor cartridge 12, said moist chambers each containing a humectant 42 specifically provided for the sensor membranes 22, 24 and respectively for the sensors 17, 18, 19, 20. Humectant 42 is provided e.g. in the form of a sponge body soaked with an electrolyte solution, or an electrolyte gel. Cup 14 further comprises in its interior a moisture absorption medium 56 which is formed e.g. by a sponge body or consists of a hygroscopic agent.

Said moist chambers 47-50 are formed by substantially cylindrical chamber walls 44 arranged vertically on the bottom 30 of cup 14. Only on the side opposite to bottom 30, said chamber walls 44 define a chamber opening 46, with the humectant 42, e.g. in the form of a sponge body or an electrolyte (not shown) inserted thereinto.

Transport container lid 16 comprises on its external side a gripping structure 52 arranged along its periphery for facilitating the gripping of lid 16. Also the transport container cup 14 comprises an external gripping structure 54 for facilitating the opening of the transport container system 10 in general.

In the transport and respectively storage condition, sensor cartridge 12 is by its flange 26 axially fixed between the flange-like lid edge 40 of lid 16 and the flange-like cup edge 32 of cup 14 so that the sensor cartridge 12 can be accommodated in the transport container cup 14 in an optimum manner, i.e. so that the distance between the sensor membranes 22, 24 and the corresponding moist chambers 47, 48 (FIG. 2) can be set in such a well-defined manner that each of the sensor membranes 22, 24 will be in optimum abutment on the humectant 42. Alternatively, a sealing ring 58 can be provided between the sensor cartridge 12 and the flange-like cup edge 32 of cup 14, allowing the transport container system 10' to be reliably closed in a liquid-tight manner.

The invention claimed is:

1. A transport container system for a water analysis sensor cartridge, the transport container comprising;
   a water analysis sensor cartridge configured to be interchangeable, the water analysis sensor cartridge comprising at least two different sensor membranes; and
   a transport container cup provided separately from the water analysis sensor cartridge, the transport container cup comprising, for each of the at least two different sensor membranes, a separate moist chamber, wherein each separate moist chamber comprises one chamber opening and a specific humectant for each of the at least two different sensor membranes, the water analysis sensor cartridge being configured to be inserted into the transport container cup.

2. The transport container system as recited in claim 1, wherein the transport container cup further comprises a bottom and a vertical chamber wall(s) arranged in a vertical orientation on the bottom, wherein each separate moist chamber is formed by a respective vertical chamber wall arranged in the vertical orientation on the bottom of the transport-container cup.

3. The transport container system as recited in claim 1, wherein the specific humectant is an electrolyte gel.

4. The transport container system as recited in claim 1, wherein the specific humectant is formed by a sponge body soaked with an electrolyte solution.

5. The transport container system as recited in claim 1, wherein the transport container cup further comprises an external side with a periphery along which a gripping structure is arranged.

6. The transport container system as recited in claim 1, wherein at least one of the at least two different sensor membranes is arranged eccentrically in the water analysis sensor cartridge.

7. The transport container system as recited in claim 1, wherein the water analysis sensor cartridge and the transport container cup are provided with cooperating anti-twist locks.

8. The transport container system as recited in claim 1, further comprising a transport container lid configured to provide for a liquid-tight closure of the transport container cup.

9. The transport container system as recited in claim 8, wherein,
   the transport container cup further comprises a transport container cup edge,
   the water analysis sensor cartridge further comprises a surrounding flange configured to be in a liquid-tight abutment on the transport container cup edge, and
   the transport container lid is formed as a fixing sleeve and is further configured to fix the water analysis sensor cartridge.

10. The transport container system as recited in claim 8, wherein the transport container cup and the transport container lid are provided with a cooperating bayonet-type lock.

11. The transport container system as recited in claim 8, wherein the transport container lid comprises an external side with a periphery along with a gripping structure is arranged.

12. The transport container system as recited in claim 1, wherein the transport container cup further comprises an interior and an absorption agent arranged in the interior.

13. The transport container system as recited in claim 12, wherein the absorption agent is formed by a sponge body.

14. The transport container system as recited in claim 12, wherein the absorption agent consists of a hygroscopic medium.

15. A transport container system for a water analysis sensor cartridge, the transport container comprising:
- a water analysis sensor cartridge configured to be interchangeable, the water analysis sensor cartridge comprising at least two different sensor membranes; and
- a transport container cup provided separately from the water analysis sensor cartridge, the transport container cup comprising,
  - a bottom,
  - a vertical chamber wall(s) arranged in a vertical orientation on the bottom, each separate moist chamber being formed by a respective vertical chamber wall arranged in the vertical orientation on the bottom of the transport-container cup, and
  - a separate moist chamber for each of the at least two different sensor membranes, each separate moist chamber comprising one chamber opening and a specific humectant for each of the at least two different sensor membranes,
  - the water analysis sensor cartridge being configured to be inserted into the transport container cup; and
- a transport container lid configured to provide for a liquid-tight closure of the transport container cup.

16. The transport container system as recited in claim 15, wherein the specific humectant is an electrolyte gel or is formed by a sponge body soaked with an electrolyte solution.

17. The transport container system as recited in claim 15, wherein,
- the transport container cup further comprises a transport container cup edge,
- the water analysis sensor cartridge further comprises a surrounding flange configured to be in a liquid-tight abutment on the transport container cup edge, and
- the transport container lid is formed as a fixing sleeve and is further configured to fix the water analysis sensor cartridge.

18. The transport container system as recited in claim 15, wherein the transport container cup and the transport container lid are provided with a cooperating bayonet-type lock.

19. The transport container system as recited in claim 15, wherein the transport container lid comprises an external side with a periphery along with a gripping structure is arranged.

20. The transport container system as recited in claim 15, wherein the transport container cup further comprises an external side with a periphery along which a gripping structure is arranged.

21. The transport container system as recited in claim 15, wherein at least one of the at least two different sensor membranes is arranged eccentrically in the water analysis sensor cartridge.

22. The transport container system as recited in claim 15, wherein the water analysis sensor cartridge and the transport container cup are provided with cooperating anti-twist locks.

23. The transport container system as recited in claim 15, wherein the transport container cup further comprises an interior and an absorption agent arranged in the interior.

24. The transport container system as recited in claim 23, wherein the absorption agent is formed by a sponge body or consists of a hygroscopic medium.

* * * * *